United States Patent [19]
Kalafus et al.

[11] 4,070,318
[45] Jan. 24, 1978

[54] POLLUTION FREE METHOD OF MAKING 2,6-BIS(2,4-DIHYDROXY PHENYLMETHYL)-4-CHLOROPHENOL TIRE CORD DIPS AND PRODUCTS

[75] Inventors: Edward F. Kalafus, Akron; Richard M. Wise, Uniontown, both of Ohio

[73] Assignee: The General Tire & Rubber Company, Akron, Ohio

[21] Appl. No.: 642,857

[22] Filed: Dec. 22, 1975

Related U.S. Application Data

[63] Continuation-in-part of Ser. No. 597,796, July 21, 1975, abandoned.

[51] Int. Cl.² .............................................. C08L 61/10
[52] U.S. Cl. ................................... 260/29.3; 428/246; 428/250; 428/252; 428/378; 428/483
[58] Field of Search ................... 260/29.3 V, 29.2 UA, 260/844, 95 C, 59 R; 428/483, 378

[56] References Cited

U.S. PATENT DOCUMENTS

| 3,547,729 | 12/1970 | Kibler | 260/29.3 |
| 3,578,613 | 5/1971 | Tai | 260/29.3 |
| 3,922,422 | 11/1975 | Wise | 260/29.3 X |
| 3,947,394 | 3/1976 | Kalafus et al. | 260/29.3 X |

Primary Examiner—Theodore E. Pertilla

[57] ABSTRACT 2,6-Bis(2,4-dihydroxy phenylmethyl)-4-chlorophenol is made by a low catalyst level process which eliminates the need to isolate the 2,6-bis hydroxymethyl-4-chlorophenol intermediate or the 2,6-bis(2,4-dihydroxy phenylmethyl)-4-chlorophenol from the reaction mixture. The 2,6-bis(2,4-dihydroxy phenylmethyl)-4-chlorophenol blended with a vinyl pyridine latex is used as a polyester cord dip. The dipped cord is used as reinforcement in rubber tires.

3 Claims, No Drawings

POLLUTION FREE METHOD OF MAKING 2,6-BIS(2,4-DIHYDROXY PHENYLMETHYL)-4-CHLOROPHENOL TIRE CORD DIPS AND PRODUCTS

CROSS-REFERENCE TO RELATED APPLICATIONS

This application is a continuation-in-part of application Ser. No. 597,796 filed July 21, 1975 now abandoned.

BACKGROUND OF THE INVENTION

The present invention is directed to a method of making an impure reaction product containing 2,6-bis(2,4-dihydroxy phenylmethyl)-4-chlorophenol and its use as a polyester cord dip. This product is made by a multistep process without isolating impurities or product. The impure reaction product is referred to herein as 2,6-bis (2,4-dihydroxy phenylmethyl)-4-chlorophenol. The prior art material is possibly also an impure reaction product. The dipped cord is used to reinforce rubber products such as tires.

Cord dips based upon the use of 2,6-bis(2,4-dihydroxy phenylmethyl)-4-chlorophenol are well known. See for example U.S. Pat. Nos. 3,660,202 Edington (1972); 3,857,730 Kalafus et al. (1974) and 3,861,980 Wise (1975); also see an article by Mather entitled "Development of a Polyester Rubber Adhesive," British Polymer Journal, Volume 3, March 1971. These cord dips are very effective and are widely used.

An experimental cord dip possibly based upon 2,6-bis(2,4-dihydroxy phenylmethyl)-4-chlorophenol made by a one-step method without isolation of product or separation of impurities may have been sampled to General Tire by ICI in 1973. The sampled ICI dip however had shortcomings and apparently never became commercial.

The Wise patent discloses the concept of using the 2,6-bis(2,4-dihydroxy phenylmethyl)-4-chlorophenol as made. While the concept is disclosed in the Wise patent, the concept disclosed is actually part of and inseparable from the invention of the present application. The best mode contemplated by the inventors named in U.S. Pat. No. 3,660,202 for making 2,6-bis(2,4-dihydroxy phenylmethyl)-4-chlorophenol is set forth as follows:

768 g. of p-cholorphenol (6.0 moles) was dissolved in 300 g. (7.5 moles) of sodium hydroxide and 1,200 ml. of water. To this solution was added 37 percent aqueous formaldehyde 1,320 ml. (16.6 moles). This solution was maintained in a thermostat bath at 37° C. for 40 hours. The precipitated sodium salt was filtered off, slurried with cold water and refiltered. The sodium salt was then dissolved in water at 90° C., acidified to pH 6.0 with glacial acetic acid, cooled to room temperature and the dimethylol derivative filtered off, and slurried with cold water until acid free.

This product was crystallized from ethyl alcohol and consisted of 2,6-bishydroxymethyl-4-chlorophenol. It had a melting point of 161°-163° C. The dimethylol derivative 2,6-bishydroxymethyl-4-chlorophenol 70 g. (0.375 mole) and resorcinol 124 g. (1.125 moles) were ground together and fused by heating at 150° C. under nitrogen in a polycondensation apparatus for 2 hours. The product was then boiled with water to remove excess resorcinol, filtered hot and dried. The product was a reddish-brown solid comprising 2,6-bis(2',4'-dihydroxy phenylmethyl)-4-chlorophenol. It was a fusible oligomer with a melting temperature of 150°-200° C. and its solubility in 5 normal aqueous ammonia was greater than 20% weight/volume.

Instead of the fusion process, the patent also contemplates a reflux method using large quantities of water with separation of the product.

As can be seen, an excess of formaldehyde is added in the first prior art step. The excess is then removed. The disposal of the removed formaldehyde will result in a disposal or a water pollution problem. The removal of the formaldehyde also results in a time consuming and expensive process step. The same can be said of the salt forming and alcohol crystallization steps. The journal reference suggests eliminating the isolation step of the intermediate but does not suggest how this is to be accomplished. The reflux process of the patent generates even more pollution. Phenolic and formaldehyde pollutants are very difficult if not impossible to remove by sewage treatment and by the water treatment normally used for drinking water supplies. This often results in off-taste and odor in drinking water. The off-taste and odor is carried over even by distillation of the polluted drinking water supply.

SUMMARY OF THE INVENTION

We have unexpectedly discovered that 2,6-bis(2,4-dihydroxy phenylmethyl)-4-chlorophenol can be made and used in a cord dip without the necessity of isolating and purifying the intermediate 2,6-bishydroxymethyl-4-chlorophenol or the 2,6-bis(2,4-dihydroxy phenylmethyl)-4-chlorophenol product. Our process constructively consumes the formaldehyde discarded by the prior art and eliminates all pollution problems caused by the prior art purification steps. Our process also eliminates the prior art purification steps and the expense incurred thereby.

DESCRIPTION OF THE PREFERRED EMBODIMENTS

The process of the present invention for making 2,6-bis(2,4-dihydroxy phenylmethyl)-4-chlorophenol comprises:

a. reacting in the presence of from about 0.05 to 0.8 mole, preferably 0.1 to 0.5, of a base catalyst,
   1. one mole of p-chlorophenol with
   2. from about 2 to 2.2 moles of formaldehyde to form a reaction mixture containing 2,6-bishydroxymethyl-4-chlorophenol
b. then without separating the 2,6-bishydroxymethyl-4-chlorophenol from the reaction mixture, adding
   1. from one to 3 moles of resorcinol and
   2. sufficient acid to neutralize the base catalyst and to lower the pH of the reaction mixture to a value of from 1 to 6 and
c. heating the mixture to form a reaction product containing 2,6-bis(2,4-dihydroxy phenylmethyl)-4-chlorophenol
d. adding base to the mixture to dissolve the 2,6-bis(2,4-dihydroxy phenylmethyl)-4-chlorophenol and to increase the pH to a value above 7
e. then without separating the 2,6-bis(2,4-dihydroxy phenylmethyl)-4-chlorophenol from the reaction mixture, adding a major amount by weight on a solids basis of an alkaline dispersion of a rubbery vinyl pyridine copolymer to a minor amount by weight on a solids basis of the reaction product containing 2,6-bis(2,4-dihydroxy phenylmethyl)-4-chlorophenol. The composition produced is a stable alkaline dispersion that can be used directly as a cord dip. Attempts at making cord dips with the prior art 2,6-bis(2,4-dihydroxy phenylmethyl)-4-chlorophenol compositions without isolation from the reaction mixture resulted in unstable dispersions.

The base catalyst preferably is selected from the group comprising sodium hydroxide, potassium hydroxide, triethylamine, and triethanol amine. The type of the basic catalyst is not critical and any of the catalysts known to be useful in the reaction between phenol and formaldehyde can be used. The pH after the addition of the base catalyst has a value of 8.5 to 11.5.

The formaldehyde can be an aqueous solution of formaldehyde or compound capable of yielding formaldehyde such as paraformaldehyde. A 10% molar excess of that required to form the dimethylol derivative of parachlorophenol is preferred. Larger excesses of formaldehyde such as described in U.S. Pat. No. 3,660,202 are undesirable and, after reaction with resorcinol, will lead to products that are insoluble in aqueous ammonia.

The acid used to neutralize the base catalyst is selected from the group comprising hydrochloric acid, sulfuric acid, chloroacetic acid, benzene sulfonic acid or other relatively strong mineral or organic acids.

The base which is added to dissolve the 2,6-bis(2,4-dihydroxy phenylmethyl)-4-chlorophenol is preferably ammonia in water solution. The pH of the solution is preferably from 9.5 to 11.

The 2,6-bis(2,4-dihydroxy phenylmethyl)-4-chlorophenol, hereafter referred to as the chlorophenolic composition is added to or mixed with the latex of the rubbery vinyl pyridine copolymer in the form of a solution 5-30% solids in water containing $NH_3$ sufficient to render the solution alkaline.

The chlorophenolic composition is heat reactable so that it can react with itself, the rubber and possibly also the cord.

Water is used in an amount sufficient to provide for the desired dispersion of the rubber or latex particles, for the solution of the heat reactable chlorophenolic composition and for the proper solids content to get the necessary pick-up of solids on and penetration between the fibers of the polyester cord.

The dip thus consists essentially of an aqueous dispersion of the rubbery vinyl pyridine copolymer latex and the heat reactable chlorophenolic composition, the copolymer and chlorophenolic composition being present in a total amount (as dry solids, dispersed or dissolved in the water) of from about 10 to 30% by weight. The ratio (dry) of the copolymer to the chlorophenolic composition in the dip is from about 100:10 to 100:75 parts by weight, preferably from about 100:15 to 100:55 parts by weight. Sufficient alkaline material is present from the chlorophenolic solution to render the dip alkaline or additional alkaline material such as $NH_4OH$ can be added to achieve this purpose, to prevent premature coagulation of the rubbery copolymer and to solubilize the chlorophenolic compound.

The type of rubber emulsion or latex preferably used in the tire cord dip bath of this invention is a latex of a copolymer of a vinyl pyrindine and a conjugated diolefin having 4 to 6 carbon atoms. The rubber latex comprises an aqueous emulsion or dispersion of a copolymer of 50 to 95 percent by weight of a conjugated diolefin having 4 to 6 carbon atoms, 5 to 40 percent of a vinyl pyrindine and 0 to 40 percent of a styrene. Examples of suitable vinyl pyridines are 2-vinyl pyridine, 4-vinyl pyridine, 2-methyl-5-vinyl pyridine and 5-ethyl-2-vinyl pyridine.

In practicing the present invention, it is usually preferred to use an emulsion or latex of a copolymer of from about 60 to 80 percent by weight of 1,3-butadiene 7 to 32 percent styrene and 7 to 22 percent of 2-vinyl pyridine. Excellent results are obtained using a latex of a terpolymer of about 70 percent by weight of 1,3-butadiene, 15 percent styrene and 15 percent 2-vinyl pyridine having a total solids content of around 30 to 50 percent by weight. Also, blends of latices may be used such as a blend of a 1,3-butadiene/2-vinyl pyridine rubbery copolymer latex and a 1,3-butadiene/styrene rubbery copolymer latex or a blend of a 1,3-butadiene/-styrene/2-vinyl pyridine rubbery copolymer latex and a 1,3-butadiene styrene rubbery copolymer latex so long as the percent by weight ratio of total monomers in the copolymers is within the ranges as specified above. The pH of the latices should be similar and the surfactants and stabilizers should be compatible to avoid coagulation on blending or mixing of the latices. The amounts of polymerization ingredients and the polymerization conditions to use are well known to the art. See "Vinyl and Related Polymers," Schildknecht, John Wiley & Sons, Inc., New York, 1952; "Synthetic Rubber," Whitby, Davis & Dunbrook, John Wiley & Sons, Inc., New York, 1954; and "Emulsion Polymerization," Bovey, Kolthoff, Medalia and Meehan, Interscience Publishers, Inc., New York, 1955. Emulsions or latices of rubbery vinyl pyridine copolymers for use in cord dips are shown by U.S. Pat. Nos. 2,561,215, 2,615,826 and 3,437,122.

In order to provide data for the tire cord adhesive of this invention, a standard single-cord H-pull test is employed to determine the static adhesion at room temperature and above of the adhesive-coated tire cord to rubber. All the data submitted herein including the examples which follow are based upon identical test conditions, and all test specimens are prepared and tested in the same way generally in accordance with ASTM Designation: D 2138-67.

In order to apply the adhesive dip to the polyester cords in a reliable manner, the cords are fed through the adhesive dip bath containing the rubber and the chlorophenolic composition and into a drying oven where they are dried. Also as the cords leave the oven they enter a cooling zone where they are air cooled. In each case the adhesive-coated cords leaving the dip are dried in the oven at from about 300° to 500° F., or at a temperature below the temperature at which the polyester of the cord would lose its tensile strength, for from about 30–150 seconds. The time the cord remains in the dip is about a second or so or at least for a period of time sufficient to allow wetting of the cord and penetration of the fibers of the cord by the adhesive mixture.

The single-cord H-pull test is then employed to determine the static adhesion of the dried adhesive coated polyester fiber cords to rubber. In each case the rubber test specimens are made from the standard type rubber composition.

| Stock | Parts By Weight |
|---|---|
| Natural Rubber (No. 3 Smoked Sheet) | 36.50 |
| Butadiene-styrene rubbery copolymer, average | |

-continued

| Stock | Parts By Weight |
|---|---|
| 23.5% bound styrene, emulsion polymerized | 43.50 |
| Polybutadiene (solution polymerized BD, about 93% cis-1,4, Raw Mooney ML-4 at 212° F. about 40-50) | 20.00 |
| Carbon black, fast extrusion furnace | 35.00 |
| Carbon black, high abrasion furnace (high structure) | 35.00 |
| Alkyl aromatic polyindene resin, reinforcing and processing aid, Picco 100, Pennsylvania Industrial Chemical Corp. | 4.5 |
| Naphthenic oil, Circosol type 2XH, Sun Oil Co. | 32.80 |
| Zinc Oxide | 3.8 |
| Stearic Acid | 1.5 |
| Mixture of mono, di and tristyrenated phenols, AgeRite Spar, R. T. Vanderbilt Co. Inc. antioxidant | 1.2 |
| Benzothiazyl disulfide, Altax, R. T. Vanderbilt Co. Inc., accelerator | 1.2 |
| Tetramethyl thiuram monosulfide, active ingredient Thionex accelerator, E. I. DuPont de Nemours & Co., Inc. | 0.1 |
| Crystex, about 80% insoluble sulfur & 20% Petroleum oil, Stauffer Chemical Co. | 3.0 |

In every case the polyester cords to be tested are placed in parallel positions in a multiple-strand mold of the type described in the single cord H-pull adhesion test designated ASTM D 2138-67, the mold is filled with unvulcanized rubber of the above composition, the cords being maintained under a tension of 50 grams each, and the rubber is cured 20 minutes at around 305° F. to the elastic state. Each rubber test specimen is ¼ inch thick and has a ⅜ inch cord embedment.

After the rubber has been cured, the hot reticulate cured rubber piece is removed from the mold, cooled and H-test specimens are cut from said piece, each specimen consisting of a single polyester cord encased in rubber and having each end embedded in the center of a rubber tab or embedment having a length of around 1 inch or so. The specimens are then aged at least 16 hours at room temperature. The force required to separate the cord from the rubber is then determined at room temperature or 250° F. using an INSTRON tester provided with specimen grips. The maximum force in pounds required to separate the cord from the rubber is the H-adhesion value.

While the adhesive containing polyester reinforcing elements of this invention can be adhered to a vulcanizable blend of natural rubber, polybutadiene rubber, and rubbery butadiene-styrene copolymer by curing the same in combination together, it is apparent that said adhesive containing polyester reinforcing element can be adhered to other vulcanizable rubbery materials by curing or vulcanizing the same in combination with the rubber, such as one or more of the foregoing rubbers as well as nitrile rubbers, chloroprene rubbers, polyisoprenes, vinyl pyridine rubbers, acrylic rubbers, isoprene-acrylonitrile rubbers and the like and mixtures of the same. These rubbers prior to curing can be mixed with the usual compounding ingredients including sulfur, stearic acid, zinc oxide, magnesium oxide, accelerators, antioxidants, antiozonants and other curatives and the like well known to those skilled in the art for the particular rubbers being employed.

Polyester fibers, yarns, filaments, cords or fabric and the like coated with the adhesive of the present invention can have from about 3 to 7% by weight (dry) total solids from the adhesive dip on the cord based on the weight of the cord and can be used in the manufacture of radial, bias, or belted-bias passenger tires, truck tires, motorcycle and bicycle tires, off-the-road tires, airplane tires, transmission belts, V-belts, conveyor belts, hose, gaskets, rubbers, tarpaulins, and the like.

The polyesters which can be used are described in detail in U.S. Pat. No. 3,861,980 of Wise (1975).

The following examples will serve to illustrate the invention with more particularity to those skilled in the art. In these examples the parts are parts by weight unless otherwise indicated.

EXAMPLE I

Into a reactor containing a stirring bar was placed 64.3 parts of p-chlorophenol, 89.2 parts of 37% formaldehyde and 4.0 parts of sodium hydroxide pellets. After solvation of the sodium hydroxide, the reactor was flushed briefly with nitrogen, capped and rotated end-over-end in a water bath at 65° C. for 6 hours. After this reaction time, the formaldehyde content had decreased from the theoretical value of 21.2% to 6.9%. The clear dark red solution became a thick slurry of solid in a few minutes. A solution of 96.3 parts of resorcinol in 125 parts of water and 9.8 parts of concentrated hydrochloric acid was added to the slurry and the mixture in the reactor was rotated in a water bath at 80° C. for 24 hours.

After reaction with resorcinol, the mixture containing much solid was treated with enough concentrated ammonium hydroxide to bring the final concentration of resin solids to 20%. The solids dissolved quite readily when the reactor was rotated in a bath at 30° C. The resulting clear, dark red solution had a Brookfield viscosity of 33.6 centipoises. The solution was perfectly compatible with vinyl pyridine latex in the amount of 47 parts of resin solids per 100 parts vinyl pyridine latex solids and this mixture when air dried produced a strong flexible film.

47 parts resin or 2,6-bis(2,4-dihydroxy phenylmethyl)-4-chlorophenol per 100 parts vinyl pyridine latex

TABLE I

COMPARISON OF H-ADHESIONS OBTAINED USING VARIOUS RESINS
(1300/3 Dacron)

| Description of Resin | H-Adhesion at RT in Stock | | | Hot H-Adhesion, Pulled at 250° F |
|---|---|---|---|---|
| | Original | Heat Aged $N_2$, 300° F/ 24 hours | Steam Aged $N_2$, 250°/ 4 hours | |
| Above resin (4 runs) | 56 | 37 | 38 | 32 |
| | 60 | 43 | 35 | 40 |
| | 62 | 47 | 37 | 39 |
| Commercial 2,6-bis(2,4-dihydroxy phenylmethyl)-4-chlorophenol (3 runs) | 62 | 46 | 36 | 39 |
| | 60 | 37 | 28 | 29 |
| | 60 | 45 | 40 | 36 |
| | 58 | 39 | 41 | 27 | solids used for dipping in all cases; 1300/3 Dacron processed at 440° F./90 seconds, 0% applied stretch.

The vinyl pyridine latex used in each case in the table was a latex of a rubbery terpolymer of 70% by weight 1,3-butadiene, 15% by weight of styrene, and 15% by weight of 2-vinyl pyridine (41% by weight solids).

EXAMPLES II THRU VIII

The following examples set forth in Table II show the effect of varying the amount of catalyst, the type of catalyst and the aging of the chlorophenolic resin solution. Except where indicated the procedure of Example I and the ingredients of Example I were used. In Example I 0.2 moles of NaOH were used per mole of p-chlorophenol.

TABLE II
EFFECT OF AMOUNT OF CATALYST ON H-ADHESION

| Type of catalyst | Moles of Catalyst per Mole of p-Chlorophenol | H-Adhesion at Room Temperature | | | Hot H-Adhesion Pulled at 250° F | Grand Avg. of the Four Categories of H-Adhesion |
|---|---|---|---|---|---|---|
| | | Original | Heat Aged, $N_2$, 300° F/24 hours | Steam Aged, $N_2$, 250° F/4 hours | | |
| 1. NaOH | 0.05 | 35 | 28 | 28 | 25 | 29.0 |
| 2. NaOH | 0.1 | 55 | 38 | 46 | 35 | 43.5 |
| 3. NaOH | 0.2* | 50 | 38 | 43 | 33 | 41.0 |
| 4. NaOH | 0.5 | 50 | 33 | 43 | 34 | 40.0 |
| 5. NaOH | 0.8 | 43 | 34 | 40 | 30 | 36.8 |
| 6. NaOH | 1.0 | 42 | 30 | 31 | 31 | 33.5 |
| 7. Triethylamine | 0.2 | 55 | 37 | 45 | 35 | 43.0 |
| 8. Triethanolamine | 0.2 | 41 | 32 | 33 | 27 | 33.3 |

*The chlorophenolic resin solution used in this example was 5 months old.

We claim:
1. A process for making a cord dip which comprises:
  a. reacting in the presence of from about 0.05 to 0.8 moles of a base catalyst
    1. one mole of p-chlorophenol with
    2. from about 2 to 2.2 moles of formaldehyde to form a reaction mixture containing 2,6-bis-hydroxymethyl-4-chlorophenol;
  b. then without separating the 2,6-bis-dihydroxymethyl-4-chlorophenol from the reaction mixture, adding
    1. from 1 to 3 moles of resorcinol and
    2. sufficient acid to neutralize the base catalyst and to lower the pH of the reaction mixture to a value of from 1 to 6;
  c. heating the mixture to form a reaction product containing 2,6-bis (2,4-dihydroxy phenylmethyl)-4-chlorophenol;
  d. adding base to the mixture to dissolve the 2,6-bis(2,4-dihydroxy phenylmethyl)-4-chlorophenol and to increase the pH to a value above 7;
  e. then without separating the 2,6-bis(2,4-dihydroxy phenylmethyl)-4-chlorophenol from the reaction mixture, adding a major amount of weight on a solid basis of an alkaline dispersion of a rubbery vinyl pyridine copolymer to a minor amount by weight on a solids basis of the reaction product containing 2,6-bis(2,4-dihydroxy phenylmethyl)-4-chlorophenol.

2. The method of claim 1 wherein from 0.1 to 0.5 mole of base catalyst is present.

3. A composition produced by the method of claim 1.

* * * * *